United States Patent
Tybinkowski et al.

(10) Patent No.: US 6,301,334 B1
(45) Date of Patent: Oct. 9, 2001

(54) BACKLASH-RESISTANT DRIVE ASSEMBLY FOR COLLIMATOR IN A CT SCANNER

(75) Inventors: Andrew P. Tybinkowski, Boxford; Ronald E. Swain, Reading; Brian M. McDermott, Tewksbury; Jonna A. Gillis, Saugus, all of MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 09/552,141

(22) Filed: Apr. 19, 2000

(51) Int. Cl.[7] .............................. G21K 1/02; F16H 55/18
(52) U.S. Cl. .............................. 378/147; 74/441; 74/409; 411/231; 378/150
(58) Field of Search ........................ 378/147, 148, 378/149, 150, 151; 74/440, 441, 409; 411/231, 273

(56) References Cited

U.S. PATENT DOCUMENTS

| 4,962,518 | * | 10/1990 | Spongr et al. | 378/148 |
| 5,054,041 | * | 10/1991 | Hampel | 378/150 |
| 5,732,596 | * | 3/1998 | Erikson et al. | 74/441 |
| 5,839,321 | * | 11/1998 | Parsons | 74/441 |

* cited by examiner

*Primary Examiner*—Drew Dunn
(74) *Attorney, Agent, or Firm*—McDermott, Will & Emery

(57) ABSTRACT

A drive assembly for a collimator of an X-ray imaging device includes a carrier which is adapted for translation in the z-direction along two parallel shafts. One of the shafts is coupled to a driver, such as a motor, by a backlash-resistant nut assembly.

7 Claims, 2 Drawing Sheets

BACKLASH-RESISTANT DRIVE ASSEMBLY FOR COLLIMATOR IN A CT SCANNER

TECHNICAL FIELD

The present invention relates to mechanical drive assemblies, and in particular to those which are used to effect precise movement of a slit plate in scanning and imaging devices.

BACKGROUND OF THE INVENTION

X-ray imaging devices generally employ a collimated beam of radiation which is directed from a focal spot through an object to be scanned, such as a live human or animal patient, or a package to be inspected. A bank of radiation-sensitive detectors is located opposite the focal spot, with the object to be scanned between the focal spot and the detectors. The focal spot and detectors may be fixed relative to one another on a gantry which rotates about the object to be scanned. The detectors receive radiation which has passed through the object and which has therefore been attenuated to varying degrees as a function of the density of structures within the object and in the radiation path. The detectors generate signals which correspond to the detected density values, and these signals are used to map the object so that the internal structures can be seen.

The radiation beam is collimated by passage of the beam through a slit in a radiation-opaque plate. Typically the plate contains a number of slits of differing widths, so that the beam can be collimated to different widths. For convenience, the slit plate is generally moved into the desired position by translation in a direction transverse to the direction of the beam (generally referred to as the z-direction).

It is important that the slit through which the radiation beam passes to be collimated be located properly relative to the focal spot and the detectors so as to admit precisely as much radiation as can be detected by the detectors, for maximum data acquisition for each scan of the object. If the slit is not properly aligned with the focal spot and the detectors, some of the radiation pass through the object but may not be received by the detectors. Any radiation which passes through the object without being detected subjects the object to radiation exposure without providing useful imaging data, and this is undesirable.

It is also important that movement of the slit plate be smooth, without backlash, accurate and precise. This is especially critical in scanners which may rotate at speeds greater than one revolution per second.

In prior art scanners, the slit plate is typically mounted on a slide which is adapted for travel along a set of parallel shafts. The slide is driven by a drive mechanism, such as a precision leadscrew, which is mounted to a stepper motor. Misalignment of the shafts, of the slide on the shafts, and binding of the leadscrew, commonly occur because it is difficult to maintain these structures in precise alignment. Because each structure is independently mounted, alignment of all three is a costly and time-consuming undertaking and must be checked and repeated frequently.

It would therefore be an advancement in the art of precision drive assemblies to overcome the disadvantages of the prior art.

SUMMARY OF THE INVENTION

According to one aspect of the invention, there is provided a backlash-resistant drive assembly, comprising a base, a first shaft secured to the base, a driver mounted to the base, a second shaft coupled to the driver and substantially parallel to the first shaft, and a carrier adapted for translation in the direction of the first and second shafts. The second shaft is coupled to the driver with a backlash-resistant nut assembly.

In one embodiment, the driver comprises a stepper motor.

The backlash-resistant nut assembly preferably comprises a first nut portion with a threaded bore, and a second nut portion having a threaded bore concentric with the threaded bore of the first nut portion, means for mutual engagement of the first and second nut portions, and a wave washer disposed between the first and second nut portions. The wave washer biases the first and second nut portions away from each other.

In one embodiment, the first nut portion is adapted for fixed engagement with the carrier.

The drive assembly may further include a bearing sleeve disposed over the first shaft and the nonthreaded portion of the second shaft and adapted for rolling engagement with the shafts and the carrier.

According to another aspect of the invention, there is provided a collimator assembly for an x-ray imaging device. The assembly comprises a base containing an aperture for passage of an x-ray beam therethrough, a backlash-resistant drive assembly affixed to the base and including a first shaft secured to the base, a driver mounted to the base, a second shaft coupled to the driver and substantially parallel to the first shaft, and a carrier adapted for translation in the direction of the first and second shafts, wherein the second shaft is coupled to the driver with a backlash-resistant nut assembly, and a slit plate fixedly mounted to the carrier and having a plurality of slits of different widths.

The collimator assembly may further include a mask plate fixed to the base beneath the carrier and over the aperture of the base, wherein the mask plate includes a single slit therein.

These and other objects and advantages of the invention will in part be obvious and will in part appear hereinafter. The invention accordingly comprises the composition and apparatus possessing the construction, combination of elements and arrangement of parts which are exemplified in the following detailed disclosure, the scope of which will be indicated in the claims.

BRIEF DESCRIPTION OF THE DRAWINGS

For a fuller understanding of the nature and objects of the present invention, reference should be had to the following detailed description taken in connection with the accompanying drawings, in which.

Like elements in the Figures are indicated by like reference numerals.

DETAILED DESCRIPTION OF THE DRAWINGS

The drive assembly of the present invention provides several advantages over prior art drive mechanisms. By combining the driving mechanism with the slide or shaft on which a driven member travels, one can eliminate relative movement between the driver and the driven member. This arrangement reduces the number of independently mounted parts which must be independently secured and provides a more smooth movement of the driven member.

Such a drive assembly is particularly useful in precision drive mechanisms, including the drive mechanisms used in imaging equipment in which beam collimation is carried out by movement of a slit plate relative to an x-ray beam. Movement of the slit plate must be accurate, repeatable and precise throughout all operating speeds and temperatures of the imaging equipment.

Figure 1:
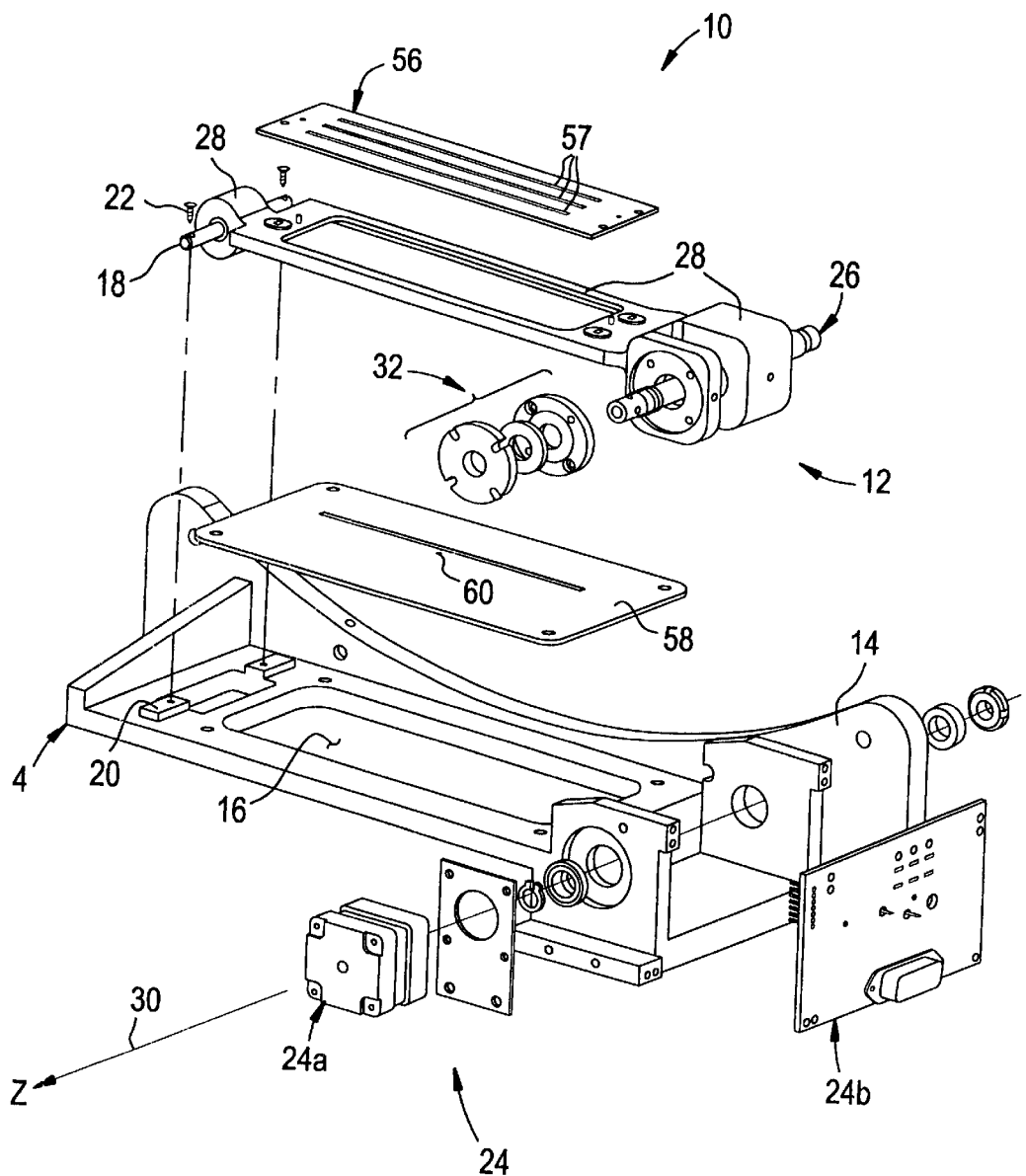
FIG. 1 is an exploded view of a collimator system of an x-ray imaging device which includes a combination slide/drive assembly according to one aspect of the present invention.

FIG. 1 illustrates a collimator assembly 10 of an x-ray imaging apparatus which includes a drive assembly 12 according to the invention. The assembly includes a base 14, which is typically made of cast and machined aluminum or brass. The base includes an aperture 16 for admission of a radiation beam from a focal spot of an x-ray source (not shown).

A first shaft 18 is secured to blocks or pads 20 at one side of the aperture on the base with screws or like fasteners 22. A driver 24, shown in FIG. 1 as a stepper motor 24a with associated controller circuitry 24b, is also mounted to the base. The driver is rotatably coupled to a second shaft 26 which is substantially parallel to the first shaft 18. A carrier 28 extends between the shafts and is disposed over the aperture 16 in the base. The carrier is adapted to slide along the shafts 18, 26 in the direction of z axis 30 and is preferably made of cast aluminum or brass.

Figure 2:
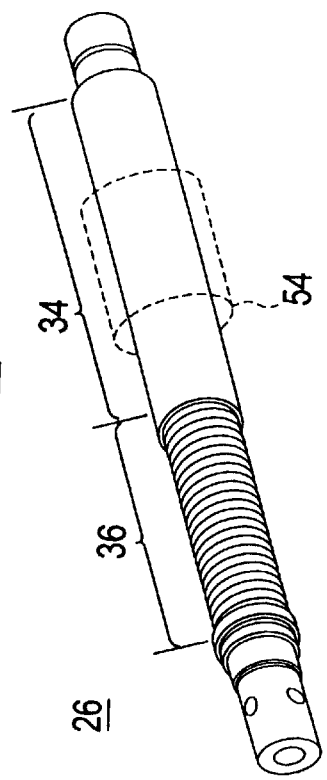
FIG. 2 is a perspective view of the second drive shaft shown in FIG. 1.

According to the invention, the second shaft 26 is coupled to the driver 24 via an backlash-resistant nut assembly 32. As shown in FIG. 2, the second shaft 26 includes a non-threaded portion 34 and a threaded portion 36. The non-threaded portion 34 of the shaft 26 is adapted for sliding engagement with the carrier, whereas the threaded portion 36 engages with the nut assembly 32, which is fixed to the carrier 28.

Figure 3:
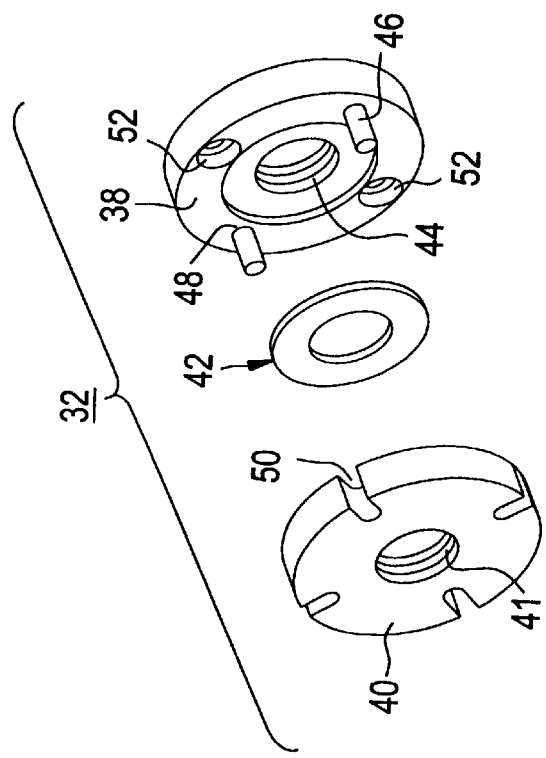
FIG. 3 is an exploded view of the backlash-resistant nut assembly shown in FIG. 1.

The nut assembly 32 is shown in FIG. 3 and includes a first nut portion 38, a second nut portion 40, and a wave washer 42 disposed between them. The first nut portion 38 has a threaded bore 44 which engages with the threaded portion 36 on the second shaft 26. The second nut portion 40 also has a threaded bore 41 which engages with the threaded portion 36 of the second shaft. The assembly also includes fasteners 46, such as dowel pins, which fit into holes 48 in the first nut portion and slots 50 in the second nut portion. The fasteners join the nut portions together around the wave washer 42, which biases the first and second nut portions away from each other. The combined tension and compression of the nut assembly which is created by the counteracting forces of the wave washer and the joined first and second nut portions eliminates substantially all play between the threads of the nut assembly and the threaded portion 36 of the second shaft and prevents any backlash in the movement of the nut over the threaded portion of the shaft 26.

The first nut portion 38 includes counterbored holes 52 for receiving fasteners or screws for joining the nut assembly to the carrier, as shown in FIG. 1. The first and second nut portions of the assembly are preferably made of a phosphor bronze material.

Figure 4:
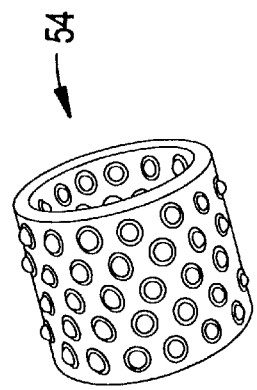
FIG. 4 is a perspective view of a ball bearing sleeve which may be used on the shafts to reduce friction.

To reduce friction and facilitate smooth movement of the carrier over the shafts, a ball bearing sleeve 54 may be disposed over each of the shafts. A typical ball bearing sleeve is illustrated in FIG. 4 and in phantom on the shaft of FIG. 2. The ball bearing sleeve 54 includes several apertures extending through the wall of the sleeve. A ball bearing is disposed in each aperture and is movable therein without becoming disengaged from the aperture, so that the ball bearing seems to float within the apertures. The ball bearings provide rolling contact between the shaft inside the sleeve and the carrier outside of the sleeve and substantially reduce the friction between these components.

The collimator assembly 10 includes a slit plate 56 which is disposed in the carrier 28 so as to be positioned over the beam aperture in the base. The slit plate 56 includes multiple slits 57 having different widths, for defining beams of different thicknesses in the z direction. The carrier and slit plate move along z axis 30 in response to travel of the nut assembly 32 over the second shaft 26.

A mask plate 58 is fixed to the base beneath the carrier 28 and is disposed over the aperture 16 in the base. The mask plate includes a single slit 60. In operation, the carrier 28 is moved in the z axis direction so that one of the slits in the slit plate 56 is aligned with the slit 60 in the mask plate, thereby allowing a collimated beam of radiation to pass through the aperture in the base to an object to be scanned and to a detector bank (not shown) beyond the object to be scanned.

Because certain changes may be made in the above apparatus without departing from the scope of the invention herein disclosed, it is intended that all matter contained in the above description or shown in the accompanying drawings shall be interpreted in an illustrative and not a limiting sense.

What is claimed is:

1. A backlash-resistant drive assembly, comprising:
   a base,
   a first shaft secured to and spaced from the base,
   a driver mounted to the base,
   a second shaft coupled to the driver and substantially parallel to the first shaft,
   a carrier adapted for translation in the direction of the first and second shafts,
   wherein the second shaft is coupled to the driver with a backlash-resistant nut assembly.

2. A drive assembly according to claim 1, wherein the driver comprises a stepper motor.

3. A drive assembly according to claim 1, wherein the backlash-resistant nut assembly comprises a first nut portion and a second nut portion, means for mutual engagement of the first and second nut portions, and a wave washer disposed between the first and second nut portions, wherein the wave washer biases the first and second nut portions away from each other.

4. A drive assembly according to claim 3, wherein the first nut portion is adapted for fixed engagement with the carrier.

5. A drive assembly according to claim 1, further including a bearing sleeve disposed over the first shaft and the nonthreaded portion of the second shaft and adapted for rolling engagement with the shafts and the carrier.

6. A collimator assembly for an x-ray imaging device, comprising:
   a base containing an aperture for passage of an x-ray beam therethrough,
   a backlash-resistant drive assembly affixed to the base and including a first shaft secured to and spaced from the base, a driver mounted to the base, a second shaft coupled to the driver and substantially parallel to the first shaft, and a carrier adapted for translation in the direction of the first and second shafts, wherein the second shaft is coupled to the driver with a backlash-resistant nut assembly, and
   a slit plate fixedly mounted to the carrier and having a plurality of slits of different widths.

7. A collimator assembly according to claim 6, further comprising a mask plate fixed to the base beneath the carrier and over the aperture of the base, wherein the mask plate includes a single slit therein.

* * * * *